(12) United States Patent
Park

(10) Patent No.: US 9,063,120 B2
(45) Date of Patent: Jun. 23, 2015

(54) DEVICE FOR MEASURING BLOOD ALCOHOL CONCENTRATION

(75) Inventor: Kwang Hee Park, Seoul (KR)

(73) Assignee: DATECH CO., LTD., Incheon (KR)

( * ) Notice: Subject to any disclaimer, the term of this patent is extended or adjusted under 35 U.S.C. 154(b) by 209 days.

(21) Appl. No.: 13/806,739

(22) PCT Filed: Jun. 8, 2011

(86) PCT No.: PCT/KR2011/004188
§ 371 (c)(1),
(2), (4) Date: Dec. 21, 2012

(87) PCT Pub. No.: WO2012/015163
PCT Pub. Date: Feb. 2, 2012

(65) Prior Publication Data
US 2013/0111979 A1    May 9, 2013

(30) Foreign Application Priority Data
Jul. 29, 2010    (KR) .................. 10-2010-0073707

(51) Int. Cl.
*G01N 33/49* (2006.01)
*G01N 1/44* (2006.01)
(Continued)

(52) U.S. Cl.
CPC ............ *G01N 33/4925* (2013.01); *A61B 5/082* (2013.01); *A61B 5/14546* (2013.01); *A61B 5/150267* (2013.01); *A61B 5/150343* (2013.01);
(Continued)

(58) Field of Classification Search
CPC ............ G01N 1/405; G01N 2001/021; G01N 2030/009; G01N 33/18; G01N 1/2035; G01N 33/4925; G01N 1/44; G01N 33/1826; A61B 5/14546; A61B 5/150267; A61B 5/150343; A61B 5/150755; A61B 5/4845; A61B 5/082
USPC ....... 73/61.59, 1.01, 1.02, 23.3, 23, 26, 27 R, 73/863.02, 864.62; 180/272, 287, 426.1, 180/426.11; 340/425.5, 426.1, 426.11; 422/58, 61, 83, 90, 98
See application file for complete search history.

(56) References Cited

U.S. PATENT DOCUMENTS 5,081,871 A * 1/1992 Glaser ....................... 73/863.23
7,993,281 B2 * 8/2011 Stock et al. ................ 600/532
(Continued)

FOREIGN PATENT DOCUMENTS

| JP | 2009-047617 | 3/2009 |
| KR | 10-1999-0037762 | 5/1999 |
| KR | 10-2010-0082538 | 7/2010 |

OTHER PUBLICATIONS

International Search Report for PCT/KR2011/004188 dated Jan. 11, 2012.

*Primary Examiner* — Daniel S Larkin
(74) *Attorney, Agent, or Firm* — Kile Park Reed & Houtteman PLLC (57) ABSTRACT

A device for measuring blood alcohol concentration for detecting the alcohol concentration from the blood of the unconscious driver as well as the driver's breath, comprises a first body including a coupling recess into which the blood collection module is coupled and a heater for heating the coupled blood collection module, and a second body including a detection probe to penetrate the blood collection module to suck the alcohol gas in the blood collection module, and an alcohol detection sensor to detect the alcohol concentration through the alcohol gas introduced through the detection probe.

4 Claims, 9 Drawing Sheets

(51) Int. Cl.
*A61B 5/145* (2006.01)
*A61B 5/15* (2006.01)
*A61B 5/157* (2006.01)
*A61B 5/00* (2006.01)
*G01N 33/497* (2006.01)
*A61B 5/08* (2006.01)
*G01N 33/18* (2006.01)

(52) U.S. Cl.
CPC ........... *A61B 5/150755* (2013.01); *A61B 5/157* (2013.01); *A61B 5/4845* (2013.01); *G01N 1/44* (2013.01); *G01N 33/18* (2013.01); *G01N 33/1826* (2013.01); *G01N 33/4972* (2013.01)

(56) References Cited

U.S. PATENT DOCUMENTS 8,455,262 B2 * 6/2013 Sultan et al. ................... 436/181
2002/0177788 A1 * 11/2002 Hodges et al. ................. 600/583
2008/0154535 A1 * 6/2008 Sparks et al. .................. 702/130

* cited by examiner

DEVICE FOR MEASURING BLOOD ALCOHOL CONCENTRATION

TECHNICAL FIELD

The present invention relates to a device for measuring blood alcohol concentration, and more particularly, to a device for measuring blood alcohol concentration for quickly and easily measuring blood alcohol concentration or blood alcohol content (BAC) of a bled unconscious examinee through blood at the site of car accident as well as the examinee's breath.

BACKGROUND ART

Usually, when the police examines whether or not a driver is drunk by using a blood alcohol testing device called a breathalyzer that is the brand name of a breath alcohol testing instrument manufacturer, the driver is made to breathe on an inlet of the blood alcohol testing device, to then enable the blood alcohol testing device to measure alcohol concentration from a breath sample and externally display a result of the measured alcohol concentration. This breath sample type alcohol testing instrument is widely used. The drivers who object to accuracy of the blood alcohol testing device are tested on whether or not they are drunk through blood collection.

However, in the case that a driver becomes unconscious due to car accident, it may not use the breath sample type blood alcohol testing device. In this case, it cannot but inevitably employ a blood sample type alcohol testing instrument that measures blood alcohol content from a blood sample through blood-gathering. It may consume a considerable amount of time and cost as well as cause tricky legal proceedings to gather blood of an unconscious person without consent. In addition, since a blood sampling approach through the blood-gathering takes a long time, it may be difficult to accurately measure blood alcohol content (BAC) at the time of the car accident. In other words, since the alcohol absorbed into the body is decomposed at a rate of 0.015%/h, it may be difficult to trust the measured blood alcohol concentration level after a long period of time has elapsed. Therefore, there is the need to quickly and accurately measure blood alcohol content (BAC) from an unconscious person at the time of the car accident.

DISCLOSURE

Technical Problem

In order to solve the above-mentioned problems of conventional art, it is an object of the present invention to provide a device for measuring blood alcohol concentration which can quickly and easily measure blood alcohol concentration of a bled unconscious examinee through blood at the site of car accident legally, as well as measure the alcohol concentration through the examinee's breath at ordinary times.

Technical Solution

To attain the above object of the present invention, according to an aspect of the present invention, there is provided a device for measuring blood alcohol concentration comprising;

a first body including a coupling recess into which the blood collection module is coupled and a heater for heating the coupled blood collection module, and a second body being formed with one body or separate body with the first body and including a detection probe to penetrate the blood collection module to suck the alcohol gas in the blood collection module, and an alcohol detection sensor to detect the alcohol concentration through the alcohol gas introduced through the detection probe.

According to another aspect of the present invention, there is provided a device for measuring blood alcohol concentration, wherein the second body is hinged on the first body and can be rotated toward the coupling recess of the first body so as for the detection probe to penetrate the blood collection module 1.

According to still another aspect of the present invention, there is provided a device for measuring blood alcohol concentration, wherein the blood concentration detection device further comprises a third body hinged on the first body or the second body and including the display to display the alcohol concentration detected by the alcohol detection sensor.

According to yet another aspect of the present invention, there is provided a device for measuring blood alcohol concentration, wherein a mouth piece mounting groove is formed on the coupling recess, into which the mouth piece having an inserting portion into which the detection probe penetrates is mounted.

According to yet another aspect of the present invention, there is provided a device for measuring blood alcohol concentration, wherein the blood collection module includes a blood collection container having an insertion portion into which the detection probe penetrates and a blood inlet holes into which the blood inflows on the outer surface of it, an absorption member to absorb the blood introduced through the blood inlet holes, and an outer container to accommodate the blood collection container.

Advantageous Effects

According to the present invention, by providing a device for measuring blood alcohol concentration having a coupling recess 82 into which the blood collection module 1 is coupled, a heater 83 for heating the coupled blood collection module 1, a detection probe 93 for penetrating the blood collection module 1 to suck the alcohol gas in the blood collection module 1, and an alcohol detection sensor 91, and by measuring the alcohol concentration of the alcohol gas introduced through the detection probe 93 from the blood collection module 1, to easily collect a blood sample from the unconscious driver at car accident site and to thus measure blood alcohol content (BAC). Accordingly, difficulties in collecting a blood sample from an unconscious person who lost consciousness due to a car accident may be solved, and blood alcohol content (BAC) may be quickly measured on the car accident spot to thus obtain a more accurate measurement value, and to thereby quickly and accurately identify car accident details.

And, by providing a device for measuring blood alcohol concentration which comprises of the first body 80 having a coupling recess 82 into which the blood collection module 1 is coupled, and the second body 90 hinged to the first body 80 and having an alcohol detection sensor 91 and the detection probe 93, measuring operation of the present invention is very easy and quick as the detection probe 93 can penetrate the blood collection module 1 by rotating the second body 90 toward the first body 80.

And as the blood collection module 1 of the present invention comprises of the blood collection container 10 containing the absorption member 20 and having the blood inlet holes 11, and the outer container 40 accommodating the blood collection container 10, police can easily collect the blood sample from the bled driver at the car accident site without cumbersome legal procedures, and the blood stained blood collection container 10 is covered by the outer container 40 to thus prevent the device for measuring blood alcohol concentration or human body from being bloodstained.

In addition, as the present invention further comprises of the mouth piece mounting groove 84 formed across the coupling recess 82 of the first body 80, into which the mouth piece 100 can be mounted, the device can also be used as an ordinary alcohol detection device using the examinee's breath as well as the blood collection means at the car accident site.

DESCRIPTION OF THE DRAWINGS

The above and other objects and advantages of the invention will become more apparent by describing a preferred embodiment with reference to the accompanying drawings in which.

DETAILED DESCRIPTION OF THE INVENTION

Hereinbelow, a device for measuring blood alcohol concentration according to a preferred embodiment of the present invention will be described with reference to the accompanying drawings.

Figure 1:
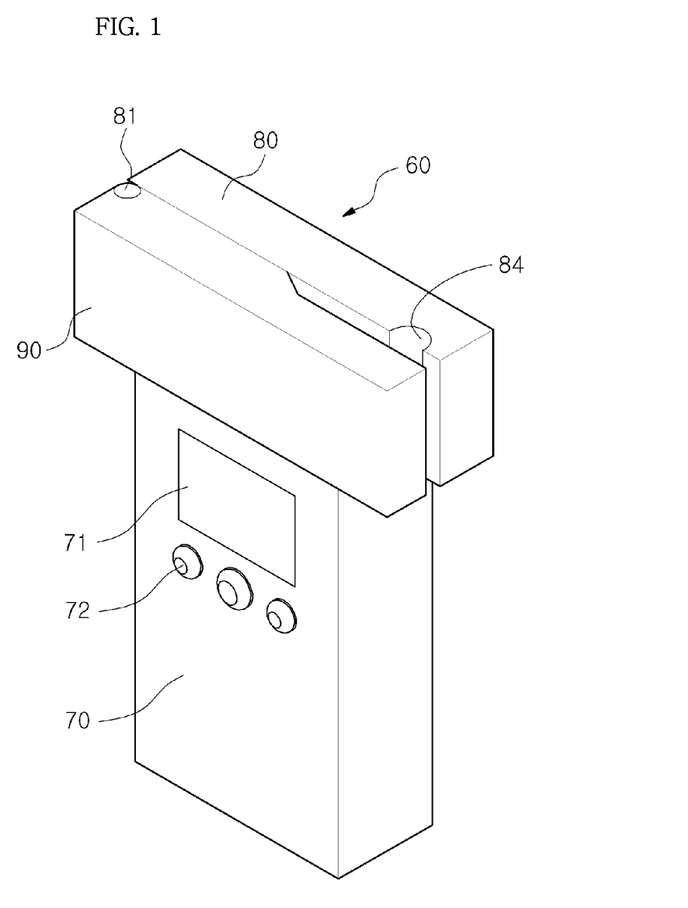
FIG. 1 is a perspective view illustrating an embodiment of the present invention.
Figure 2:
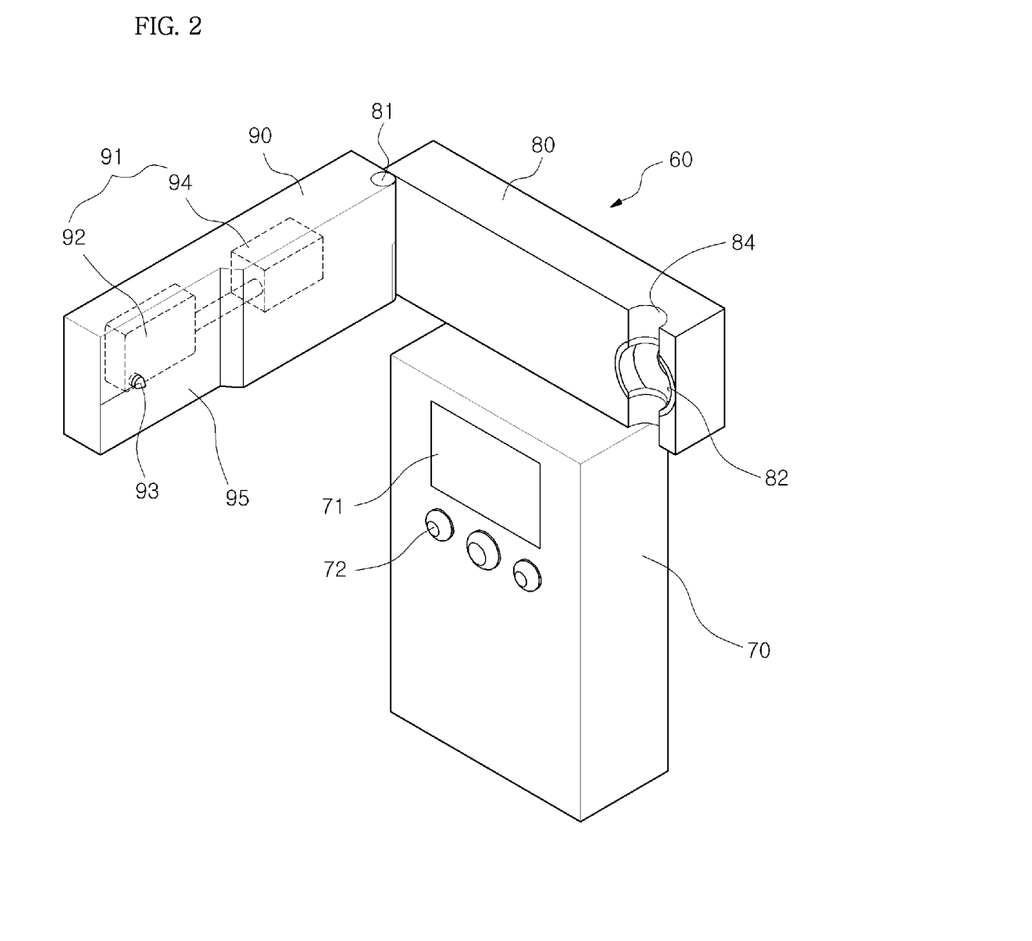
FIG. 2 is a perspective view illustrating an embodiment of the present invention in the state of the second body is opened.

A device for measuring blood alcohol concentration according the present invention is a device to detect the blood alcohol concentration from the driver's breath as well as the driver's blood bled at the car accident site. As shown in FIG. 1 and FIG. 2, the device for measuring blood alcohol concentration 60 of the present invention comprises a first body 80 including a coupling recess 82 into which the blood collection module 1 is coupled, a second body 90 hinged on the first body 80 to rotate toward the coupling recess 82 of the first body 80 and including the alcohol detection sensor 90, and a third body 70 engaged with the first body 80 and having a display 71 to display the detected alcohol concentration values.

The first body 80 is formed in the rectangular shape and the coupling recess 82 is formed on the inner surface of it. The first body 80 further includes a heater 83 to heat the coupling recess 82. The heater 83 heats the blood in the blood sample collecting module 1 coupled in the coupling recess 82 to the temperature of that of human body to evaporate the alcohol contents in the blood into the alcohol gas. The first body 80 also includes a mouth piece mounting groove 84 crossing the coupling recess 82 vertically.

The second body 90 is also formed in the rectangular shape and one end of it is hinged to the first body 80 at the hinge part 81, and the second body 90 can be folded to the first body 80 and locked by the locking member (not shown). The second body 90 includes the alcohol detecting sensor 91 which comprises a sensor module 92 to detect the blood alcohol content (BAC) and the measuring module 94 to output the detected signal with the predetermined electrical level. A detection probe 93 is projected from the sensor module 92 toward the coupling recess 82 of the first body 80. A stepped portion 95 is formed on the second body 90 facing the coupling recess 82 of the first body 80.

The top surface of the third body 70 is engaged with the bottom surface of the first body 80, and the third body 70 includes the display 71 to display the values of the detected alcohol concentration and the key button 72.

Figure 4:
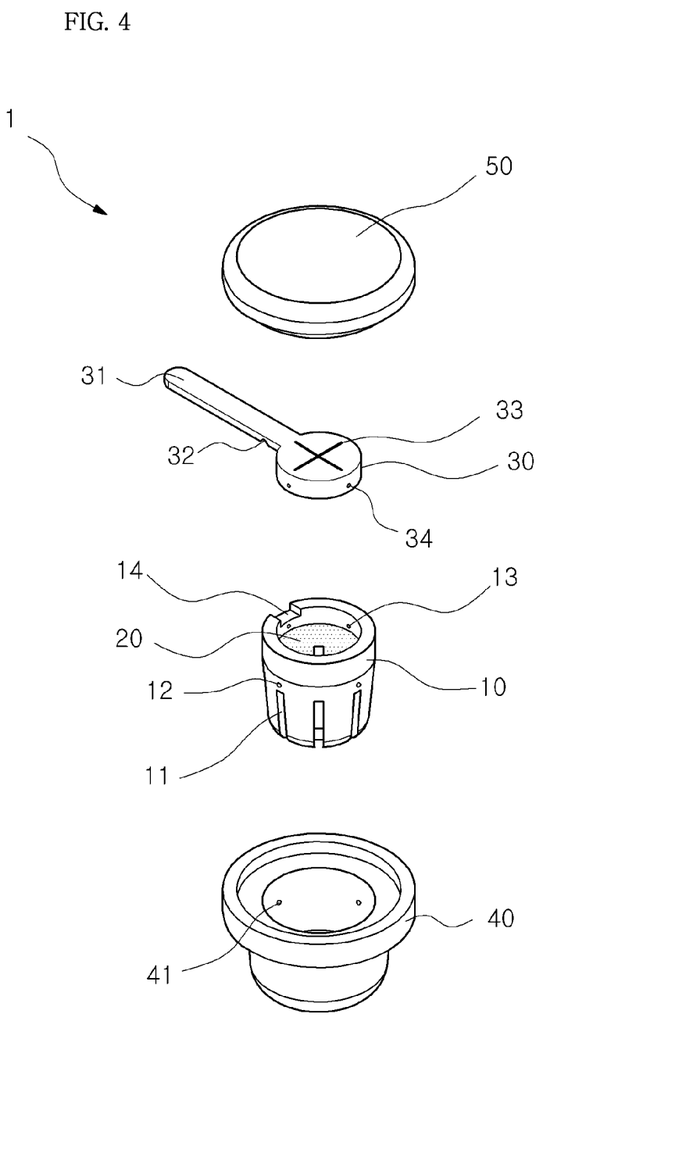
FIG. 4 is an exploded view of the blood collection module.
Figure 5:
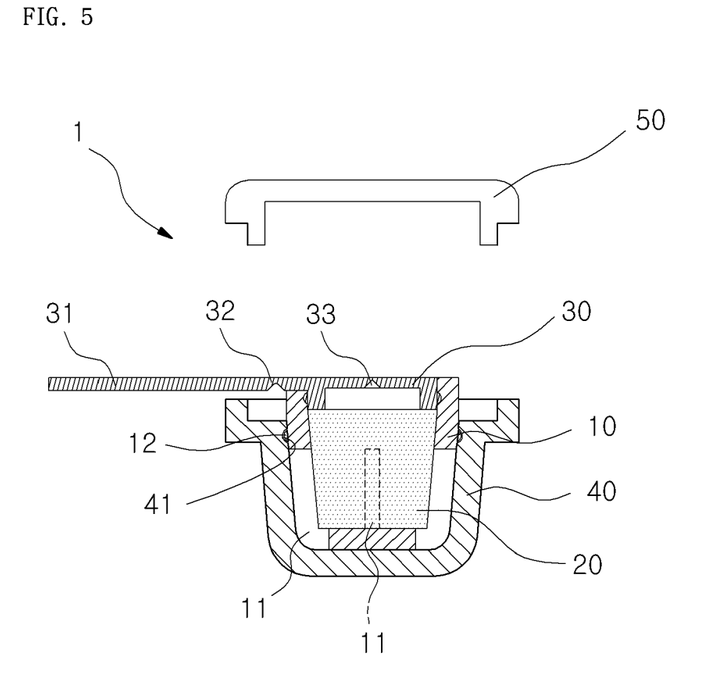
FIG. 5 is a sectional view of the blood collection module.

The blood collection module 1 is coupled into the coupling recess 82 of the first body 80. The module 1 comprises of a blood collection container 10, a absorption member 20 provided in the blood collection container 10, and an outer container 40 to accommodate the blood collection container 10. The blood collection container 10 is a vessel with the top surface open. A fitting groove 14 is formed on one side of the upper portion of the blood collection container 10, and a plurality of blood inlet holes 11 are formed along the circumferential direction on the outer surface of the blood collection container 10. The blood inlet holes 11 are shown in the form of an up-and-down elongate hole, respectively, but are not limited thereto. Any shapes of the blood inlet holes through which blood can be easily absorbed will suffice. In addition, a plurality of holding grooves 13 are formed on the upper portion of the inner surface of the blood collection container 10.

A container cover 30 having a handle 31 in which a tear-off portion 32 is formed is coupled on the upper surface of the blood collection container 10. The handle 31 is inserted into the fitting groove 14. A plurality of stop protrusions 34 that are stopped by the holding grooves 13 of the blood collection container 10, are formed along the circumferential surface of the container cover 30. Accordingly, the container cover 30 is fixedly coupled with the blood collection container 10. In addition, the inserting portion 33 that is inserted by the detection probe 93 of the second body 90 is formed on the container cover 30. The inserting portion 33 may be formed of a variety of shapes and materials, for example, may be formed of a thin film structure that may be easily bored. In addition, the inserting portion 33 may be implemented into a pattern such as '+' or 'x' in the form of a plurality of slits or score lines, so that the detection probe 93 can easily penetrate the central portion of the intersection of the inserting portion 33. Therefore, the container cover 30 enables the detection probe 93 to be easily inserted into the blood collection container 10 while preventing the collected blood from leaking.

A plurality of fixing protrusions 12 are formed along the circumferential direction on the outer surface of the upper portion of the blood collection container 10. The container cover 30 is formed separately from the blood collection container 10 in the present embodiment, but alternatively the container cover 30 may be integrally formed with the blood collection container 10.

The absorption member 20 is made of a material that may quickly absorb blood such as a sponge and cotton cloth. Moreover, an absorbent may be added to the absorption member 20 to absorb blood more quickly and strongly. The absorption member 20 is filled in the inside of the blood collection container 10.

Meanwhile, the blood collection container 10 is accommodated in the outer container 40, and a plurality of fixing grooves 41 are formed along the circumferential direction on the upper portion of the inner surface of the outer container 40. Therefore, when the blood collection container 10 is inserted into the outer container 40, the fixing protrusions 12 of the blood collection container 10 are fitted into the fixing grooves 41 of the outer container 40 and thus the blood collection container 10 is fixed to the outer container 40. Accordingly, when blood is collected with the blood collection container 10, the blood stained on the outer surface of the blood collection container 10 is isolated from the outside. As a result, when the blood collection container 10 is inserted into the coupling recess 82 of the device for measuring blood alcohol concentration 60, the device for measuring blood alcohol concentration 60 may be prevented from being bloodstained.

Meanwhile, the blood collection container 10 may be coupled with the outer container 40 in a press fit structure. However, in the case that the blood collection container 10 is pressed, blood collected in the blood collection container 10 may be pushed out. Accordingly, it is desirable that the blood collection container 10 is coupled with the outer container 40, in a coupling structure by using the fixing protrusions 12 and the fixing grooves 41. In addition, a cover member 50 that seals the outer container 40 is provided. Accordingly, after the blood alcohol content (BAC) is completely measured through the device for measuring blood alcohol concentration 60, the blood collection container 10 is put into the inside of the outer container 40 to then seal the outer container 40. Accordingly, blood may be prevented from being deteriorated and smell may be blocked.

Figure 3:
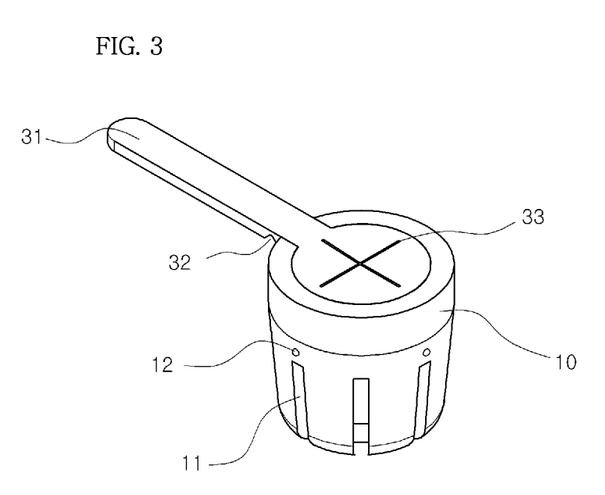
FIG. 3 is a perspective view of the blood collection module with the outer container being removed.

Operations of collecting a blood sample and measuring a blood alcohol content (BAC) through the device for measuring blood alcohol concentration having the above-described structure according to an embodiment of the present invention, will be described below. Referring to FIG. 3 showing a state where the outer container 40 and the cover member 50 are removed from the blood collection container 10, first an examiner holds the handle 31 of the container cover 30 and makes the blood collection container 10 contact blood bled by the examinee, then the blood may be introduced into the inside of the blood collection container 10 through the blood inlet holes 11 formed in the blood collection container 10. The introduced blood is absorbed in the absorption member 20 filled in the blood collection container 10. In addition, in the case that the outer surface of the blood collection container 10 is bloodstained, the examiner or the device for measuring blood alcohol concentration 60 may be bloodstained. Thus, to prevent this, the blood collection container 10 is put into the outer container 40 and then the handle 31 of the container cover 30 is torn off at the tear-off portion 32 to be removed from the container cover 30.

Figure 6:
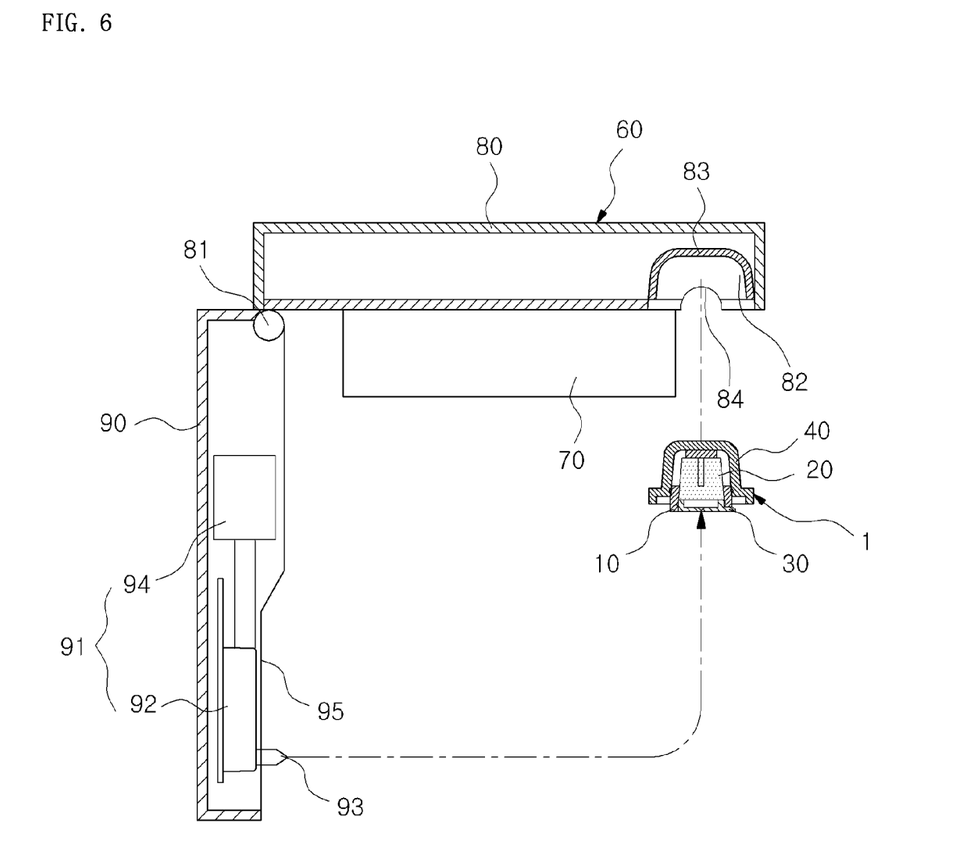
FIG. 6 is a view of the blood collection module being coupled into the device for measuring blood alcohol concentration.
Figure 7:
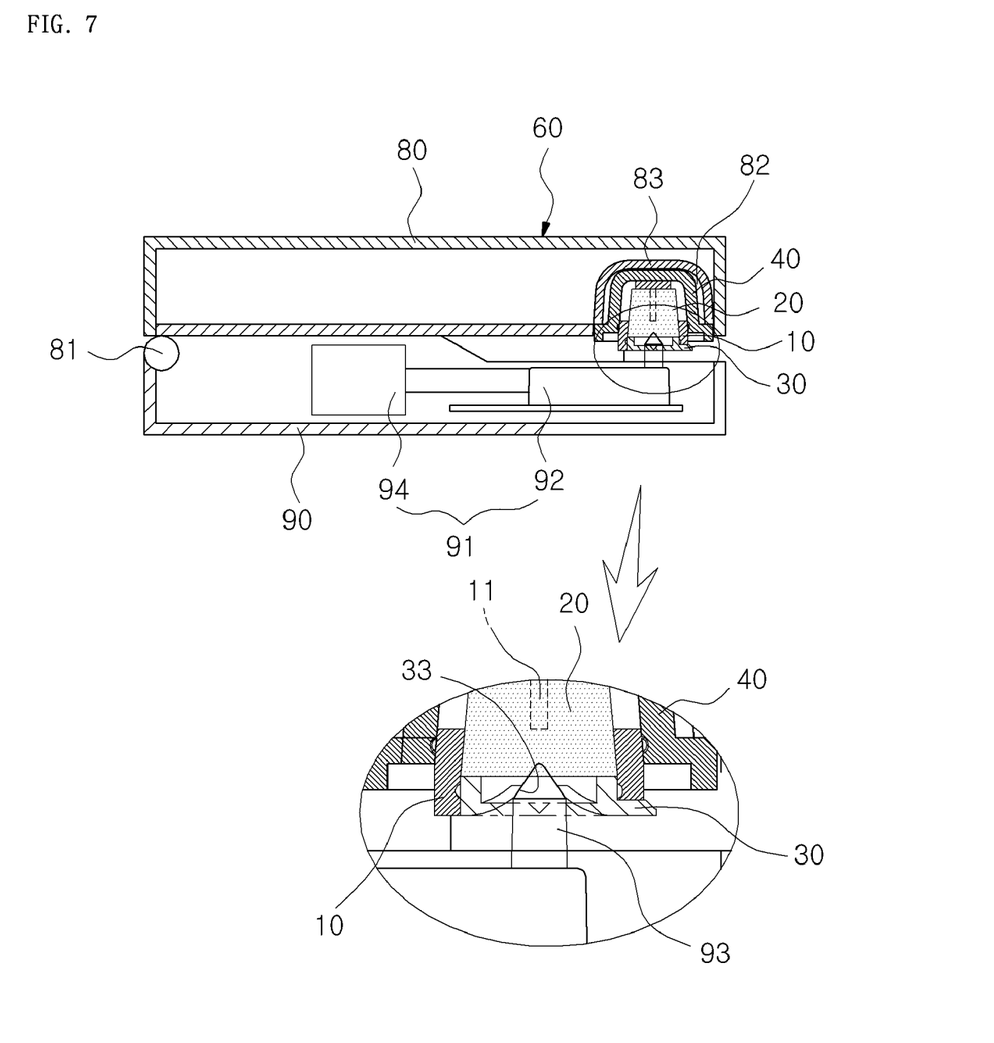
FIG. 7 is a view of the blood collection module having been coupled into the device for measuring blood alcohol concentration.
Figure 8:
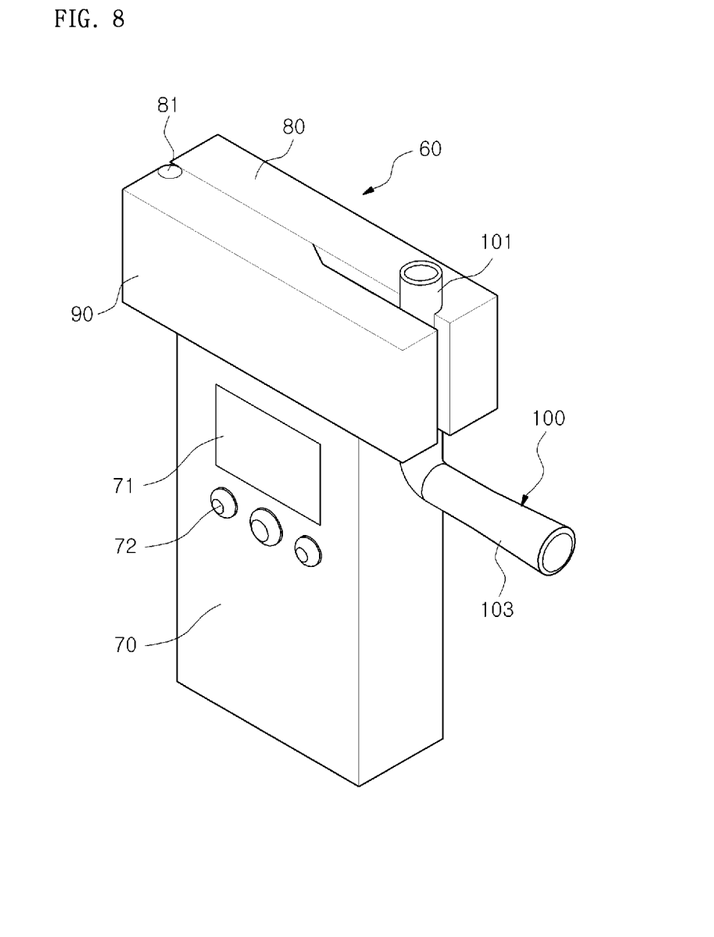
FIG. 8 a perspective view illustrating the mouth piece being mounted on the device for measuring blood alcohol concentration.
Figure 9:
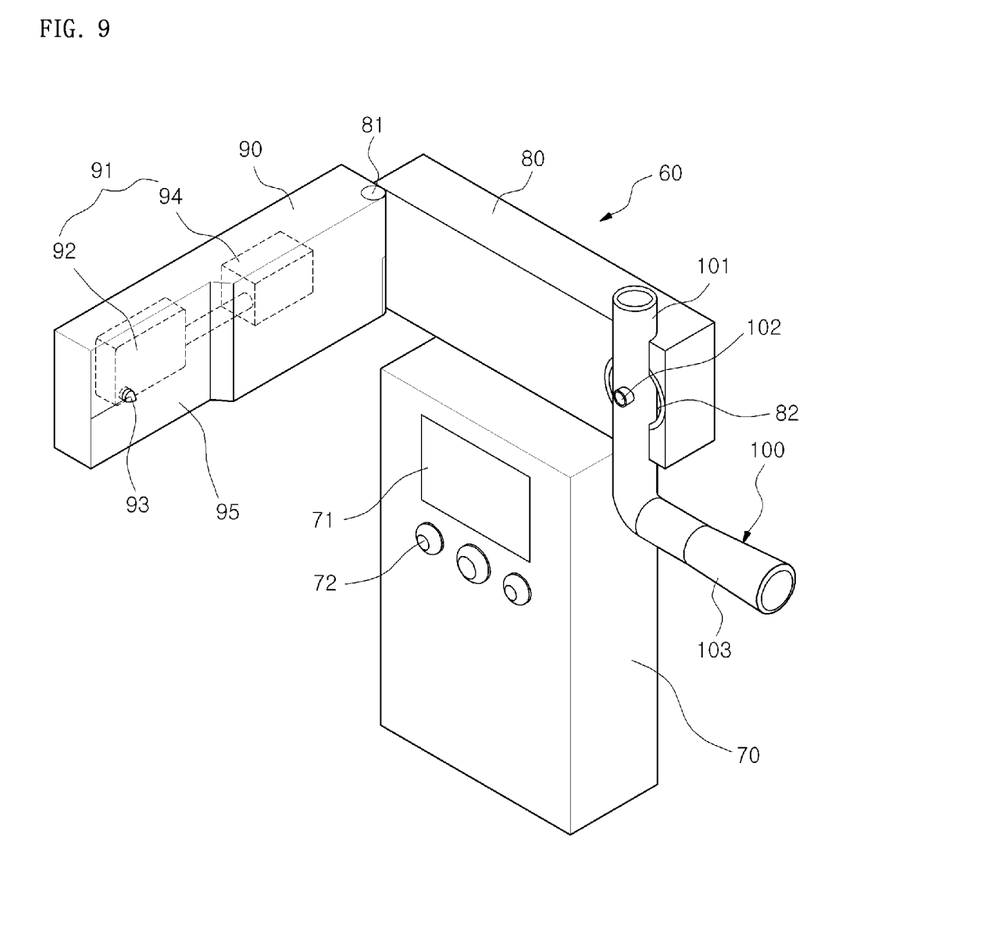
FIG. 9 is a perspective view illustrating the mouth piece being mounted on the device for measuring blood alcohol concentration and the second body being opened.

Thereafter, the outer container 40 into which the blood collection container 10 has been inserted is fitted into the coupling recess 82 of the first body 80, and then the second body 90 is rotated toward the first body 80. Accordingly, the detection probe 93 of the second body 90 penetrates the inserting portion 33 of the container cover 30 attached on the blood collection container 10 to then be advanced into the blood collection container 10. Then, blood contained in the blood collection container 10 is heated by the heater 83 to thus generate an alcohol gas. Then, the generated alcohol gas is introduced into the alcohol detection sensor 91 through the detection probe 93, to thus make it possible to measure a blood alcohol content (BAC) in the measuring module 93 and to display the measurement value on the display 71.

As described above, according to the present invention, blood bled by an unconscious person who lost consciousness on an accident spot may be legally and quickly collected through the blood collection container 10, without passing through a complicated procedure for collecting a blood sample with no consent of the unconscious person. In addition, blood alcohol content (BAC) may be measured directly from the blood sample through the device for measuring blood alcohol concentration 60, to thus reduce an error due to a delay in time and to thereby measure accurate blood alcohol content (BAC). Meanwhile, the device for measuring blood alcohol concentration 60 that has been described in the present embodiment is only an example, and alternatively various shapes of device for measuring blood alcohol concentrations having a detection probe that is inserted into the blood collection container 10 may be applied in the present invention.

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

The invention claimed is:

1. A device for measuring blood alcohol concentration comprising;
    a first body including a coupling recess into which the blood collection module is coupled and a heater for heating the coupled blood collection module, and
    a second body being formed with one body or separate body with the first body and including a detection probe to penetrate the blood collection module, wherein the second body is hinged on the first body and can be rotated toward the coupling recess of the first body so as for the detection probe to penetrate the blood collection module to suck the alcohol gas in the blood collection module, and an alcohol detection sensor to detect the alcohol concentration through the alcohol gas introduced through the detection probe.

2. The device for measuring blood alcohol concentration according to claim 1, wherein the blood concentration detection device further comprises a third body hinged on at least one of said first body and said second body and including a display to display the alcohol concentration detected by the alcohol detection sensor.

3. The device for measuring blood alcohol concentration according to claim 1, wherein a mouth piece mounting groove is formed on the coupling recess, into which the mouth piece having an inserting portion into which the detection probe penetrates is mounted.

4. The device for measuring blood alcohol concentration according to claim 1, wherein the blood collection module includes a blood collection container having an insertion portion into which the detection probe penetrates and a blood inlet holes into which the blood inflows on the outer surface of it, an absorption member to absorb the blood introduced through the blood inlet holes, and an outer container to accommodate the blood collection container.

* * * * *